United States Patent
Thong et al.

(10) Patent No.: US 6,934,582 B2
(45) Date of Patent: Aug. 23, 2005

(54) APPARATUS FOR TREATING FIBRILLATION OF AT LEAST ONE CHAMBER OF A HEART

(75) Inventors: Tran Thong, Portland, OR (US); Indra B. Nigam, Tigard, OR (US); Mrigank Shekhar, Vancouver, WA (US); Max Schaldach, deceased, late of Erlangen (DE); by Max Schaldach, Jr., legal representative, Berlin (DE)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 565 days.

(21) Appl. No.: 10/017,998

(22) Filed: Dec. 13, 2001

(65) Prior Publication Data
US 2002/0120300 A1 Aug. 29, 2002

(30) Foreign Application Priority Data
Dec. 18, 2000  (DE) ........................................ 100 64 597

(51) Int. Cl.$^7$ ................................................ A61N 1/39
(52) U.S. Cl. ................................. 607/5; 607/6; 607/7
(58) Field of Search .......................................... 607/4–7

(56) References Cited

U.S. PATENT DOCUMENTS

| | | | |
|---|---|---|---|
| 4,895,151 A | 1/1990 | Grevis ............................ | 607/4 |
| 5,441,519 A * | 8/1995 | Sears ............................. | 607/5 |
| 5,662,689 A * | 9/1997 | Elsberry et al. ................ | 607/5 |
| 5,843,134 A | 12/1998 | Thong ......................... | 318/468 |
| 5,999,851 A * | 12/1999 | White ............................ | 607/5 |
| 6,018,681 A | 1/2000 | Kim ............................... | 607/5 |
| 6,068,651 A * | 5/2000 | Brandell ........................ | 607/5 |
| 6,091,989 A | 7/2000 | Swerdlow ...................... | 607/5 |
| 6,091,991 A | 7/2000 | Warren ......................... | 607/14 |
| 6,115,633 A | 9/2000 | Lang ............................ | 607/17 |
| 6,134,470 A | 10/2000 | Hartlaub ....................... | 607/14 |
| 6,298,267 B1 * | 10/2001 | Rosborough et al. .......... | 607/6 |
| 6,356,785 B1 * | 3/2002 | Snyder et al. ................. | 607/5 |
| 6,618,617 B2 * | 9/2003 | Chen et al. .................... | 607/5 |
| 2003/0078621 A1 * | 4/2003 | Ujhelyi et al. ................. | 607/5 |

FOREIGN PATENT DOCUMENTS

| | | | | |
|---|---|---|---|---|
| DE | 38 23 969 A1 | 2/1989 | ......... | A61N/1/365 |
| DE | 196 09 409 C2 | 9/1997 | ......... | A61N/1/365 |
| DE | 196 54 494 A1 | 5/1998 | ......... | A61N/1/365 |
| EP | 0 594 271 * | 9/1993 | ......... | A61N/1/39 |
| EP | 0 838 234 A | 4/1998 | ......... | A61N/1/39 |

\* cited by examiner

Primary Examiner—Carl H. Layno
(74) Attorney, Agent, or Firm—Hahn Loeser + Parks LLP

(57) ABSTRACT

Apparatus for treating fibrillation of at least one chamber of a heart comprising a fibrillation detector for detecting a fibrillation, a defibrillator for defibrillating the chamber of the heart, wherein the defibrillator is connected to the fibrillation detector and is adapted to effect defibrillation subsequently to a time interval after detection of the fibrillation, a warning device which is connected to the fibrillation detector and which is adapted to delivery a warning signal when a fibrillation has been detected, and a control circuit having a control input actuable by a patient, wherein the control circuit is connected to the defibrillator and is adapted to delay the time of a defibrillation if the control circuit receives a corresponding signal by way of the control input, wherein the apparatus includes a condition detector which is adapted to detect a hemodynamic condition of the heart, and the control circuit is connected to the condition detector and is adapted to prevent a delay in the time of defibrillation when the condition detector detects a predetermined hemodynamic condition.

66 Claims, 1 Drawing Sheet

APPARATUS FOR TREATING FIBRILLATION OF AT LEAST ONE CHAMBER OF A HEART

The invention concerns an apparatus for treating fibrillation of at least one chamber of a heart comprising a fibrillation detector for detecting a fibrillation, a defibrillator for defibrillating the chamber of the heart, wherein the defibrillator is connected to the fibrillation detector and is adapted to effect defibrillation subsequently to a time interval after detection of the fibrillation, a warning device which is connected to the fibrillation detector and which is adapted to delivery a warning signal when a fibrillation has been detected, and a control means having a control input actuable by a patient, wherein the control means is connected to the defibrillator and is adapted to delay the time of a defibrillation if the control means receives a corresponding signal by way of the control input.

Fibrillation counts amongst cardiac disrhythmia and denotes irregular and unco-ordinated contraction of the muscle fibers of the heart. A distinction is made between atrial and ventricular fibrillation, depending on whether the fibrillation occurs in the atrium or the ventricle of a heart. Atrial fibrillations count among the cardiac disrhythmia which most frequently occur. However, they are not directly life-threatening so that treatment does not have to be implemented immediately. U.S. Pat. No. 6,068,651 to Pacesetter Inc. therefore proposes an implantable apparatus for the treatment of fibrillations, having a patient control means which allows the patient to control the time of defibrillation treatment. The patient is firstly informed by means of a warning device that a condition of atrial fibrillation is occurring. The patient then has the option, during a predetermined period of time, of himself initiating defibrillation of the atrium or further delaying the time of defibrillation. A surprising and possibly painful onset of a fibrillation treatment can thus be avoided for the patient.

However, having the time for treatment of a fibrillation determined by a patient can entail risks. For, atrial fibrillation can give rise to ventricular fibrillation as time passes or may even involve such an increase that the patient is acutely endangered. In addition, it can be accompanied by ventricular tachycardia, which is also not without its dangers for the patient.

SUMMARY OF THE INVENTION

Therefore, the object of the present invention is to provide an apparatus for treating fibrillation of at least one chamber of a heart, of the kind set forth in the opening part of this specification, which obviates the foregoing disadvantages.

The apparatus for treating a fibrillation in accordance with accompanying claim 1 attains that object. The apparatus includes a fibrillation detector for detecting a fibrillation, a defibrillator for defibrillating the chamber of the heart, wherein the defibrillator is connected to the fibrillation detector and is adapted to effect defibrillation subsequently to a time interval after detection of the fibrillation, a warning device which is connected to the fibrillation detector and which is adapted to delivery a warning signal when a fibrillation has been detected, and a control means having a control input actuable by a patient, wherein the control means is connected to the defibrillator and is adapted to delay the time of a defibrillation if the control means receives a corresponding signal by way of the control input. In addition the apparatus according to the invention is characterized in that it includes a condition detector which is adapted to detect a hemodynamic condition of the heart, and the control means is connected to the condition detector and is adapted to prevent a delay of the time of defibrillation if the condition detector detects a predetermined hemodynamic condition. The patient is still in a position to delay the moment of defibrillation, by means of the control means. That occurs however only if the condition detector does not detect a predetermined hemodynamic condition. The term predetermined hemodynamic conditions is used to denote such conditions which require early or immediate treatment of the heart. If the condition detector detects such a hemodynamic condition, the control means does not permit a delay in defibrillation. Defibrillation is therefore implemented, even if the patient seeks to delay it. In principle it is therefore possible for the patient to delay the time of defibrillation. If however the patient is acutely endangered, defibrillation takes place without delay. That means that the patient is still allowed to determine the time of defibrillation without however having to accept the patient being jeopardized.

Preferably, the fibrillation detector is adapted to detect atrial fibrillation and the defibrillator is adapted to treat atrial fibrillation. Atrial fibrillations are generally not critical so that it is appropriate to afford a patient the option of shifting the time of treatment of fibrillation of that nature. A prerequisite in that respect is that the apparatus according to the invention is enabled to detect and treat atrial fibrillation. If however atrial fibrillation brings about the predetermined hemodynamic condition, the control means prevents the fibrillation treatment from being delayed.

Preferably, the fibrillation detector is adapted to detect ventricular fibrillation and the defibrillator is preferably also adapted to treat ventricular fibrillation. It is thus possible to recognize and treat both ventricular and also atrial fibrillation conditions.

The warning device is preferably connected to the condition detector and is adapted to deliver a first warning signal when the predetermined hemodynamic condition and a fibrillation were detected, and a second warning signal when no predetermined hemodynamic condition and a fibrillation were detected. Defibrillation of the heart is effected without delay if the predetermined hemodynamic condition and fibrillation are detected. The first warning signal therefore advises the patient that defibrillation is immediately imminent. The patient also knows that delay in the treatment is out of the question. The second warning signal indicates that there is fibrillation which can be delayed. For, the delay in fibrillation is not prevented by the control means if the situation does not involve a predetermined hemodynamic condition. Therefore the two different warning signals notify the patient of his condition. He can thus better prepare himself and his surroundings for the treatment.

The defibrillator is preferably adapted to deliver a pain killer and/or a sedative or tranquilizer prior to defibrillation. Additionally or alternatively the apparatus for treating fibrillation may also include a pain therapy unit which is connected to the control means and to nerve electrodes and is adapted to output by way of the nerve electrodes electrical pulses which are suitable for numbing pain sensations. Defibrillation of the heart is generally highly painful to the patient and in addition it represents an unusual and disquieting situation for the patient, in which the patient is exposed from time to time to not inconsiderable pain levels. Administration of pain killers and tranquilizers can prevent the patient going into a critical, stress-induced shock condition.

The condition detector is preferably adapted to ascertain the predetermined hemodynamic condition on the basis of one or more indicators. For that purpose the condition detector is preferably connected to the fibrillation detector and is adapted to detect ventricular fibrillation as one of the indicators or the indicator. Ventricular fibrillations are extremely dangerous to life and result in death after a short period of time. They accordingly indicate a condition which requires immediate treatment. When the condition detector recognizes the presence of ventricular fibrillation, it can prevent a delay in defibrillation of the ventricle. In addition, the condition detector is preferably adapted to detect heart output, as the indicator or as one of the indicators. Heart output gives the volume of blood which the heart pumps through the body per unit of time. A sharp drop in heart output results in the body being inadequately supplied with blood, which finally can result in death. Accordingly heart output is an important indicator in regard to the hemodynamic condition of the patient. If the heart output falls below a given predetermined threshold value the control means can prevent a delay in defibrillation. Preferably heart output is detected by means of epicardial or intracardial impedance measurements by the condition detector. Impedance measurement involves using at least two electrodes, by which an alternating current is passed through the tissue. While the alternating current is flowing through the tissue there is a potential difference between the electrodes, which is proportional to the impedance of the electrodes. The current flows preferably through body material with a high level of conductivity such as blood. Less current flow through muscles which involve a medium level of conductivity while fat, air and bone involve a very low level of conductivity. In addition impedance is a function of the conductivity and the cross-sectional area of the conducting body. Therefore, impedance measurements between electrodes which are fixed epicardially or endocardially to the heart make it possible to measure the volume of blood which is in the chamber of the heart. The cyclic changes in the impedance of the heart are thus to be attributed to filling and emptying of the chambers of the heart. That therefore affords a measurement in respect of heart output. Finally the condition detector is preferably adapted to detect a blood pressure as the indictor or as one of the indicators. As is known blood pressure is a measurement in respect of the hemodynamic condition of the patient.

Preferably the apparatus for treating fibrillation—in particular the control means—has means for manually initiating atrial fibrillation by the patient even for the situation where the fibrillation detector has not yet detected fibrillation. That makes it possible for the patient to initiate atrial defibrillation of his own accord, if he feels unwell and for example has feelings of dizziness which point to atrial fibrillation to which the fibrillation detector has not yet responded.

BRIEF DESCRIPTION OF THE DRAWINGS

A preferred embodiment by way of example of the present invention will be described hereinafter with reference to the accompanying FIGURE in which.

DETAILED DESCRIPTION OF THE INVENTION

Figure 1:
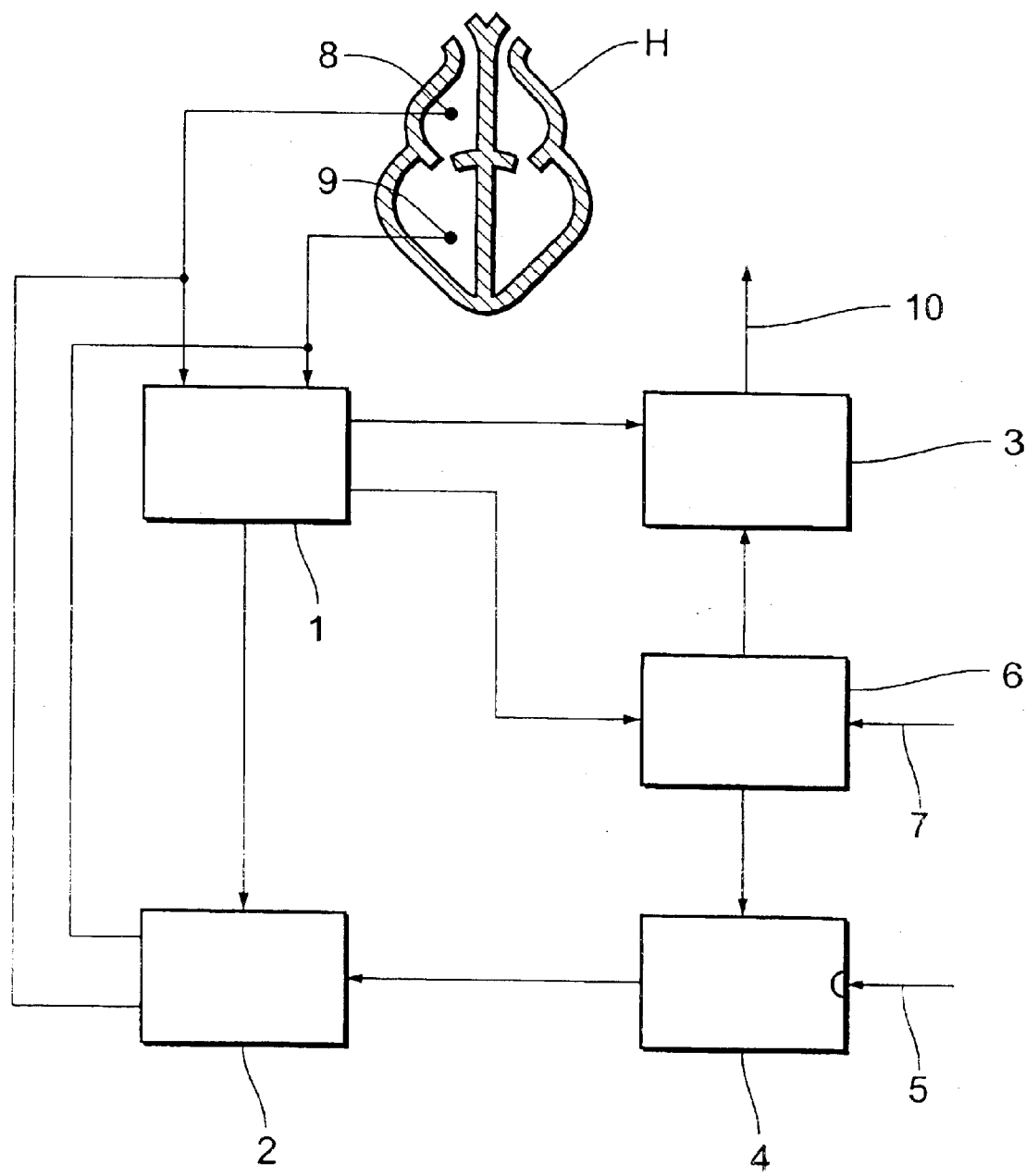
FIG. 1 shows an apparatus for treating fibrillation of at least one chamber of a heart in accordance with the first embodiment of the present invention.

Reference numeral 1 denotes a fibrillation detector in FIG. 1. It has two inputs for the connection of a respective electrode which are placed in the ventricle and in the atrium of the heart to be monitored. The electrical signals originating from the ventricle and the atrium respectively of the heart characterize the activity of the atrium or the ventricle respectively. The fibrillation detector 1 is adapted to detect fibrillation of the atrium or ventricle on the basis of the electrical signals received by way of the respective inputs.

The fibrillation detector 1 is connected on the output side to a defibrillator 2 and to electrodes 8 and 9. By way of the electrodes 8 and 9, the fibrillation detector 1 receives electrical signals from a heart H, which in the manner of an electrocardiogram can characterize fibrillation of the atrium or ventricle. The fibrillation detector 1 is also connected to a warning device 3 and sends a signal to the warning device 3 when it detects atrial or ventricular fibrillation.

The fibrillation detector 1 is also connected to a condition detector 6 which receives a signal from the fibrillation detector 1 when it detects a ventricular fibrillation. Such a signal in turn causes the condition detector 6 to transmit a signal to the warning device 3, to which it is also connected.

If the warning device 3 receives substantially at the same time a signal from the condition detector 6 and the fibrillation detector 1, it delivers a first warning signal to the patient. Electrical or acoustic signals can serve as the warning signal, the warning signal must be such that it can be at least perceived by the patient. The first warning signal signals both the presence of a fibrillation and also a critical condition. Ventricular fibrillation is generally critical for a patient so that the warning device 3 delivers the first warning signal to the patient when ventricular fibrillation occurs. If however the warning device 3 receives only one signal from the fibrillation detector 1, it outputs a second warning signal. That signals to the patient the presence of fibrillation but not a critical condition.

The condition detector 6 may also have further inputs, by way of which it receives signals 7 which indicate a critical hemodynamic condition of the patient. The condition detector 6 sends a signal both to the warning device 3 and also to a control means 4 to which it is connected, when a predetermined hemodynamic condition is detected.

The control means 4 has a control input 5 for receiving control signals. The control signals can be of electrical, electromagnetic or acoustic nature. The control means 4 is also connected to the defibrillator 2. When the control means 4 receives a signal from the condition detector 6, it does not send a signal to the defibrillator 2, irrespective of whether a signal was received at the same time by way of the control input. The defibrillator 2 is again connected to the electrodes 8 and 9 which are in the atrium and the ventricle of the heart H. The defibrillator 2 is also connected to the fibrillation detector 1. The fibrillation detector 1 signals to the defibrillator 2 whether there is an atrial and/or ventricular fibrillation. When the defibrillator 2 receives such a signal from the fibrillation detector 1 and no signal from the control means 4, it sends electrical pulses 8 and 9 by way of the electrodes to the atrium or ventricle in order to defibrillate same. When there is an atrial fibrillation but no ventricular fibrillation, only the atrium is defibrillated by the defibrillator 2. The defibrillator 2 behaves in a corresponding manner, when ventricular fibrillation is involved. If however the defibrillator 2 receives a signal from the control means 4, it delays the output of the electrical pulses for defibrillation purposes by a certain period of time. That period of time is encoded in the signal received from the control means and is read by the defibrillator 2.

What is claimed is:

1. An apparatus for treating fibrillation of at least one chamber of a heart of a patient, comprising:

a fibrillation detector;

a defibrillator for defibrillating the chamber of the heart, wherein the defibrillator is connected to the fibrillation detector and effects defibrillation subsequently to a time interval after detection of the fibrillation;

a warning device which is connected to the fibrillation detector that delivers a warning signal when a fibrillation has been detected; and a control means for controlling the apparatus having a control input actuable by the patient, wherein the control means is connected to the defibrillator and delays the time of a defibrillation if the control means receives a corresponding signal by way of the control input, characterized in that the apparatus further comprises a condition detector that detects a hemodynamic condition of the heart, and the control means is connected to the condition detector and prevents a delay in the time of defibrillation when the condition detector detects a predetermined hemodynamic condition.

2. The apparatus of claim 1, wherein:
the fibrillation detector is adapted to detect atrial fibrillation and
the defibrillator is adapted to treat atrial fibrillation.

3. The apparatus of claim 2, wherein:
the fibrillation detector is further adapted to detect ventricular fibrillation.

4. The apparatus of claim 3, wherein:
the defibrillator is further adapted to treat ventricular fibrillation.

5. The apparatus of claim 4, wherein:
the warning device is connected to the condition detector and outputs a first type of said warning signal when both the predetermined hemodynamic condition and the fibrillation are detected, and outputs a second type of warning signal when the fibrillation is detected with no predetermined hemodynamic condition.

6. The apparatus of claim 5, wherein:
the defibrillator delivers a pain killer and/or a tranquilizer prior to defibrillation.

7. The apparatus of claim 5, further comprising:
a pain therapy unit which is connected to the control means and to nerve electrodes and which delivers electrical pulses for numbing pain sensations by way of the nerve electrodes.

8. The apparatus of claim 2, wherein:
the warning device is connected to the condition detector and outputs a first type of said warning signal when both the predetermined hemodynamic condition and the fibrillation are detected, and outputs a second type of said warning signal when the fibrillation is detected with no predetermined hemodynamic condition.

9. The apparatus of claim 8, further comprising:
a pain therapy unit which is connected to the control means and to nerve electrodes and which delivers electrical pulses for numbing pain sensations by way of the nerve electrodes.

10. The apparatus of claim 8, wherein:
the defibrillator delivers a pain killer and/or a tranquilizer prior to defibrillation.

11. The apparatus of claim 2, wherein:
the defibrillator delivers a pain killer and/or a tranquilizer prior to defibrillation.

12. The apparatus of claim 2, further comprising:
a pain therapy unit which is connected to the control means and to nerve electrodes and which delivers electrical pulses for numbing pain sensations by way of the nerve electrodes.

13. The apparatus of claim 2, wherein:
the condition detector ascertains the predetermined hemodynamic condition on the basis of one or more indicators.

14. The apparatus of claim 13, wherein:
the condition detector detects a blood pressure as the indicator or as one of the indicators.

15. The apparatus of claim 14, further comprising:
means for manually initiating atrial defibrillation from outside the body, said means being at least indirectly connected to the defibrillator, for the patient to initiate defibrillation even if the fibrillation detector has not yet detected fibrillation.

16. The apparatus of claim 13, wherein:
the condition detector detects heart output as the indicator or as one of the indicators.

17. The apparatus of claim 16, wherein:
the condition detector detects a blood pressure as the indicator or as one of the indicators.

18. The apparatus of claim 17, further comprising:
means for manually initiating atrial defibrillation from outside the body, said means being at least indirectly connected to the defibrillator, for the patient to initiate defibrillation even if the fibrillation detector has not yet detected fibrillation.

19. The apparatus of claim 16, wherein:
the condition detector detects heart output by means of epicardial or endocardial impedance measurements.

20. The apparatus of claim 19, wherein:
the condition detector detects a blood pressure as the indicator or as one of the indicators.

21. The apparatus of claim 20, further comprising:
means for manually initiating atrial defibrillation from outside the body, said means being at least indirectly connected to the defibrillator, for the patient to initiate defibrillation even if the fibrillation detector has not yet detected fibrillation.

22. The apparatus of claim 1, wherein
the fibrillation detector is adapted to detect ventricular fibrillation.

23. The apparatus of claim 22 wherein:
the defibrillator is adapted to treat ventricular fibrillation.

24. The apparatus of claim 23, wherein:
the warning device is connected to the condition detector and outputs a first type of said warning signal when both the predetermined hemodynamic condition and the fibrillation are detected, and outputs a second type of said warning signal when the fibrillation is detected with no predetermined hemodynamic condition.

25. The apparatus of claim 24, wherein:
the defibrillator delivers a pain killer and/or a tranquilizer prior to defibrillation.

26. The apparatus of claim 24, further comprising:
a pain therapy unit which is connected to the control means and to nerve electrodes and which delivers electrical pulses for numbing pain sensations by way of the nerve electrodes.

27. The apparatus of claim 22, wherein:

the warning device is connected to the condition detector and outputs a first type of said warning signal when both the predetermined hemodynamic condition and the fibrillation are detected, and outputs a second type of said warning signal when the fibrillation is detected with no predetermined hemodynamic condition.

28. The apparatus of claim 27, wherein:

the defibrillator delivers a pain killer and/or a tranquilizer prior to defibrillation.

29. The apparatus of claim 27, further comprising:

a pain therapy unit which is connected to the control means and to nerve electrodes and which delivers electrical pulses for numbing pain sensations by way of the nerve electrodes.

30. The apparatus of claim 22, wherein:

the defibrillator delivers a pain killer and/or a tranquilizer prior to defibrillation.

31. The apparatus of claim 22, further comprising:

a pain therapy unit which is connected to the control means and to nerve electrodes and which delivers electrical pulses for numbing pain sensations by way of the nerve electrodes.

32. The apparatus of claim 22, wherein:

the condition detector ascertains the predetermined hemodynamic condition on the basis of one or more indicators.

33. The apparatus of claim 32, wherein:

the condition detector detects a blood pressure as the indicator or as one of the indicators.

34. The apparatus of claim 33, further comprising:

means for manually initiating atrial defibrillation from outside the body, said means being at least indirectly connected to the defibrillator, for the patient to initiate defibrillation even if the fibrillation detector has not yet detected fibrillation.

35. The apparatus of claim 32, wherein:

the condition detector is connected to the fibrillation detector and detects ventricular fibrillation as the indicator or as one of the indicators.

36. The apparatus of claim 35, wherein:

the condition detector detects a blood pressure as the indicator or as one of the indicators.

37. The apparatus of claim 36, further comprising:

means for manually initiating atrial defibrillation from outside the body, said means being at least indirectly connected to the defibrillator, for the patient to initiate defibrillation even if the fibrillation detector has not yet detected fibrillation.

38. The apparatus of claim 35, wherein:

the condition detector detects heart output as the indicator or as one of the indicators.

39. The apparatus of claim 38, wherein:

the condition detector detects heart output by means of epicardial or endocardial impedance measurements.

40. The apparatus of claim 39, wherein:

the condition detector detects a blood pressure as the indicator or as one of the indicators.

41. The apparatus of claim 40, further comprising:

means for manually initiating atrial defibrillation from outside the body, said means being at least indirectly connected to the defibrillator, for the patient to initiate defibrillation even if the fibrillation detector has not yet detected fibrillation.

42. The apparatus of claim 38, wherein:

the condition detector detects a blood pressure as the indicator or as one of the indicators.

43. The apparatus of claim 42, further comprising:

means for manually initiating atrial defibrillation from outside the body, said means being at least indirectly connected to the defibrillator, for the patient to initiate defibrillation even if the fibrillation detector has not yet detected fibrillation.

44. The apparatus of claim 32, wherein:

the condition detector detects heart output as the indicator or as one of the indicators.

45. The apparatus of claim 44, wherein:

the condition detector detects a blood pressure as the indicator or as one of the indicators.

46. The apparatus of claim 45, further comprising:

means for manually initiating atrial defibrillation from outside the body, said means being at least indirectly connected to the defibrillator, for the patient to initiate defibrillation even if the fibrillation detector has not yet detected fibrillation.

47. The apparatus of claim 44, wherein:

the condition detector detects heart output by means of epicardial or endocardial impedance measurements.

48. The apparatus of claim 47, wherein:

the condition detector detects a blood pressure as the indicator or as one of the indicators.

49. The apparatus of claim 48, further comprising:

means for manually initiating atrial defibrillation from outside the body, said means being at least indirectly connected to the defibrillator, for the patient to initiate defibrillation even if the fibrillation detector has not yet detected fibrillation.

50. The apparatus of claim 1, wherein:

the warning device is connected to the condition detector and outputs a first type of said warning signal when the predetermined hemodynamic condition and a fibrillation are detected, and to outputs a second type of said warning signal when the fibrillation is detected with no predetermined hemodynamic condition.

51. The apparatus of claim 50, wherein:

the defibrillator delivers a pain killer and/or a tranquilizer prior to defibrillation.

52. The apparatus of claim 50, further comprising:

a pain therapy unit which is connected to the control means and to nerve electrodes and which delivers electrical pulses for numbing pain sensations by way of the nerve electrodes.

53. The apparatus of claim 1, wherein:

the defibrillator delivers a pain killer and/or a tranquilizer prior to defibrillation.

54. The apparatus of claim 53, further comprising:

a pain therapy unit which is connected to the control means and to nerve electrodes and which delivers electrical pulses for numbing pain sensations by way of the nerve electrodes.

55. The apparatus of claim 1, further comprising:

means for manually initiating atrial defibrillation from outside the body, said means being at least indirectly connected to the defibrillator, for the patient to initiate defibrillation even if the fibrillation detector has not yet detected fibrillation.

56. The apparatus of claim 55, wherein:

the control means includes the means for manual initiation of atrial defibrillation.

57. The apparatus of claim 1, further comprising:

a pain therapy unit which is connected to the control means and to nerve electrodes and which delivers electrical pulses for numbing pain sensations by way of the nerve electrodes.

58. The apparatus of claim 1, wherein:

the condition detector ascertains the predetermined hemodynamic condition on the basis of one or more indicators.

59. The apparatus of claim 58, wherein:

the condition detector detects a blood pressure as the indicator or as one of the indicators.

60. The apparatus of claim 59, further comprising:

means for manually initiating atrial defibrillation from outside the body, said means being at least indirectly connected to the defibrillator, for the patient to initiate defibrillation even if the fibrillation detector has not yet detected fibrillation.

61. The apparatus of claim 58, wherein:

the condition detector detects heart output as the indicator or as one of the indicators.

62. The apparatus of claim 61, wherein:

the condition detector detects a blood pressure as the indicator or as one of the indicators.

63. The apparatus of claim 62, further comprising:

means for manually initiating atrial defibrillation from outside the body, said means being at least indirectly connected to the defibrillator, for the patient to initiate defibrillation even if the fibrillation detector has not yet detected fibrillation.

64. The apparatus of claim 61, wherein:

the condition detector detects heart output by means of epicardial or endocardial impedance measurements.

65. The apparatus of claim 64, wherein:

the condition detector detects a blood pressure as the indicator or as one of the indicators.

66. The apparatus of claim 65, further comprising:

means for manually initiating atrial defibrillation from outside the body, said means being at least indirectly connected to the defibrillator, for the patient to initiate defibrillation even if the fibrillation detector has not yet detected fibrillation.

* * * * *